United States Patent [19]
Alfano et al.

[11] Patent Number: 5,849,595
[45] Date of Patent: Dec. 15, 1998

[54] METHOD FOR MONITORING THE EFFECTS OF CHEMOTHERAPEUTIC AGENTS ON NEOPLASMIC MEDIA

[76] Inventors: Robert R. Alfano, 3777 Independence Ave., Bronx, N.Y. 10463; Guichen C. Tang, 2670 Valentine Ave., Bronx, N.Y. 10458; Stimson P. Schantz, 78 Honey Hollow Rd., Pound Ridge, N.Y. 10576

[21] Appl. No.: 537,591

[22] Filed: Oct. 2, 1995

Related U.S. Application Data

[63] Continuation of Ser. No. 102,094, Aug. 6, 1993, abandoned, which is a continuation-in-part of Ser. No. 956,750, Oct. 5, 1992, abandoned.

[51] Int. Cl.⁶ .................................................. G01N 21/00
[52] U.S. Cl. ........................... 436/164; 426/63; 426/64; 426/805; 426/811; 426/813; 422/82.07
[58] Field of Search ............... 436/64, 164, 63, 436/805, 811, 813; 422/82.06, 82.07, 82.11

[56] References Cited

U.S. PATENT DOCUMENTS

| | | | |
|---|---|---|---|
| 4,310,546 | 1/1982 | Gander | 424/311 |
| 4,930,516 | 6/1990 | Alfano et al. | |
| 4,957,114 | 9/1990 | Zeng et al. | |
| 4,977,276 | 12/1990 | Berlin et al. | 549/58 |
| 4,981,783 | 1/1991 | Augenlicht | 435/6 |
| 5,008,291 | 4/1991 | Minton et al. | 514/578 |
| 5,042,494 | 8/1991 | Alfano | |
| 5,094,783 | 3/1992 | Muccio et al. | 260/413 |
| 5,131,398 | 7/1992 | Alfano et al. | |

FOREIGN PATENT DOCUMENTS 2-22331  7/1983  Japan.

OTHER PUBLICATIONS

Sacks, "Growth of Head and Neck Squamous Cell Carcinoma Cell Lines as Multicell Tumor Spheroids," Head and Neck Oncology Research Proceedings of the IInd Int'l. Head and Neck Oncology Research Conf., G.T. Wolf and T.E. Carey, ed., Kugler Publ., Amsterdam, pp. 3–9 (1987).

Lippman et al., Cancer Treatment Reports, vol. 71, No. 5 (May 1987).

*Primary Examiner*—Lien Tran
*Attorney, Agent, or Firm*—Kriegsman & Kriegsman

[57] ABSTRACT

A method for monitoring the effects of a chemotherapeutic agent on a neoplasm medium. The method is premised on the discovery that chemotherapeutic agent, such as retinoic acid, affects the fluorescence spectroscopy of neoplasmic media and that such differences can be monitored, for example, by comparing the spectral profiles, spectral peaks, and spectral bandwidths of fluorescence at various wavelengths of the medium before and after administration of the chemotherapeutic agent. Differences in the excitation spectroscopy of the medium can also be used to monitor the effects of the agent.

18 Claims, 16 Drawing Sheets

METHOD FOR MONITORING THE EFFECTS OF CHEMOTHERAPEUTIC AGENTS ON NEOPLASMIC MEDIA

This application is a continuation of application Ser. No. 08/102,094 filed on Aug. 6, 1993 now abandoned, which is a continuation-in-part application of presently U.S. patent application Ser. No. 07/956,750, filed Oct. 5, 1992 abandoned.

BACKGROUND OF THE INVENTION

The present invention relates to a method and system for monitoring the effects of chemotherapeutic agents on neoplasmic media.

Chemotherapy is an approach widely used by the medical community to kill cancerous cells and to inhibit the growth of cancer. As can readily be appreciated, it would be highly desirable for one to be able to monitor the effects of a chemotherapeutic agent on a neoplasmic medium, e.g., to determine the efficacy of the agent.

Retinoic acid is a chemical that is currently being explored as a preventive and therapeutic agent for certain cancers. One of the cancers on which retinoic acid is currently being investigated is squamous cell carcinoma of the upper aerodigestive tract. This type of cancer occurs in approximately 40,000 individuals per year.

Other chemical agents are currently being investigated for use with other cancers or are currently being used in the treatment and/or prevention of certain cancers. Examples of such chemical agents include indoles, polyacetylenes, terpenoids, quinones, isolflavones, thioallyl, caratenoids, diallyl sulfide/disulfide, phenethyl isothiocyanate, indole-3-carbinol, and glutathione. These agents apparently function through their antioxidant and free radical suppressing properties.

SUMMARY OF THE INVENTION

It is an object of the present invention to provide a technique for monitoring the effects of a chemotherapeutic agent on a neoplasmic medium.

The present invention is premised on the discovery that the administration of one or more chemotherapeutic agents, such as retinoic acid, indoles, polyacetylenes, terpenoids, quinones, isoflavones, thioallyl, caratenoids, diallyl sulfide/disulfide, phenethyl isothiocyanate, indole-3-carbinol and glutathione, to a neoplasmic medium brings about a change in the fluorescence properties of certain fluorophores present within the medium. Accordingly, by comparing the fluorescence properties of the medium before and after administration of the chemotherapeutic agent(s) thereto, one can monitor the effects of the agent(s) on the medium. The aforementioned comparison may comprise comparing the fluorescence spectra of the medium before and after administration of the agent(s) or may comprise comparing predetermined spectral peaks or bandwidths. Alternatively, excitation spectra, peaks or bandwidths may be compared instead of emission spectra, peaks and bandwidths.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
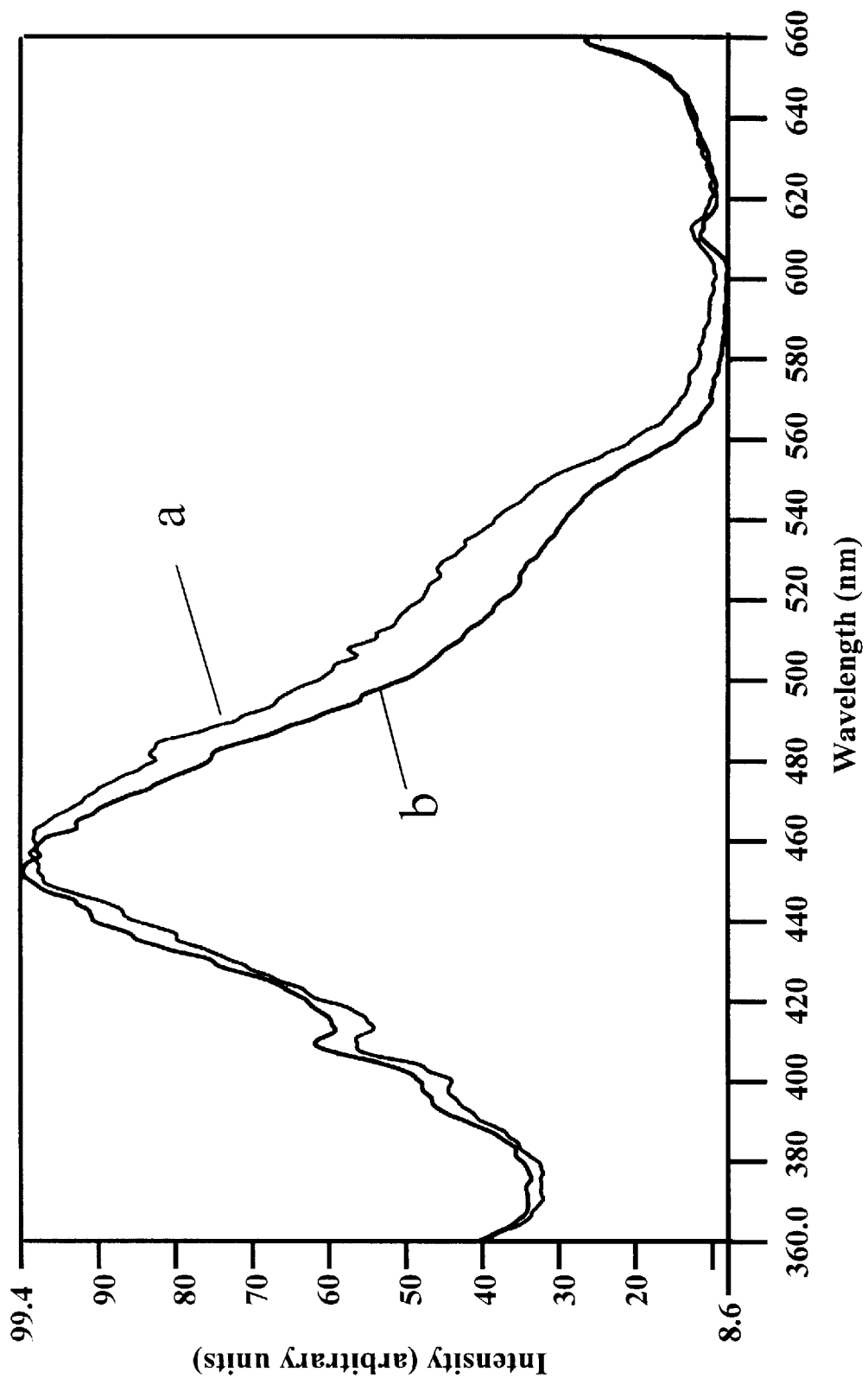
FIG. 1 is a graphic representation of the fluorescence spectra obtained when 340 nm light was used to excite the RA treated MTS (curve a) and the control MTS (curve b)
Figure 1A:
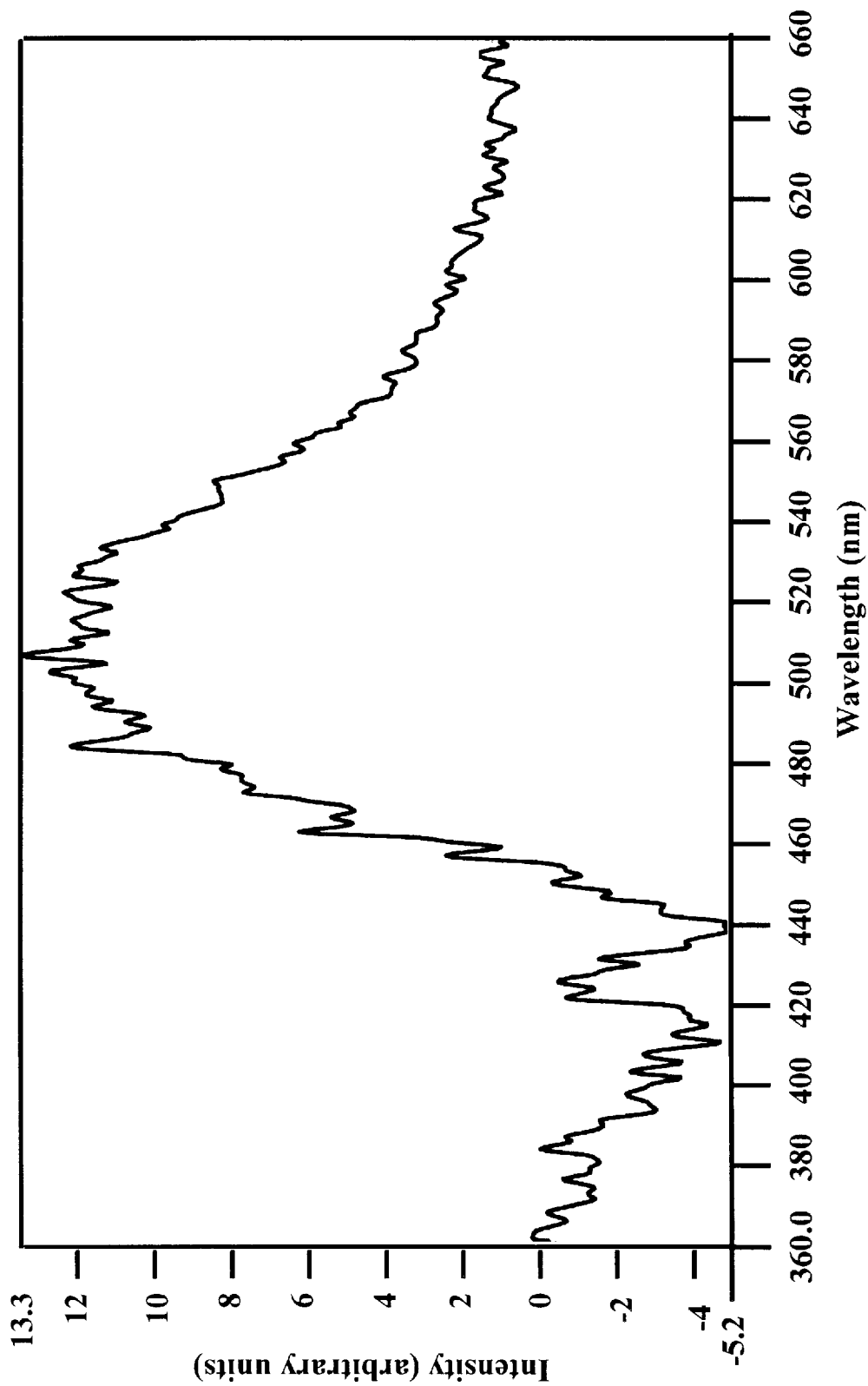
FIG. 1(a) is a graphic representation of the difference between curves a and b of FIG. 1 after they have been normalized to the same intensity.

The above-described fluorescence technique was tested on squamous cell (MDA886). MDA886 can be grown as a multicellular tumor spheroid (MTS). Unlike monolayer cultures, MTS display biologial properties that are similar to in vivo tumors. As the spheroid size increases, the center becomes necrotic due to gradient effects and limited diffusion of metabolites such as oxygen and glucose. For this reason, these samples provide an ideal experimental model to investigate the antitumor effect of retinoids and demonstrate the concept of using fluorescence as a marker to determine if chemicals are working. As will be seen below, it was found that fluorescence spectroscopic methods permit one to detect the molecular changes and the spectral differences between the control and retinoic acid (RA) chemical treated spheroids. These spectroscopic changes can then be used to develop biological endpoint markers of alternations in the cancer site. Fluorescence spectroscopy from tissue can be used to determine changes of the fluorphors treated by chemicals and drugs and evaluate changes occuring in the therapy of cancers.

The established cancer cell line MDA 886L was used in this study. The samples were obtained from Dr. Schantz, Drs. Pinto and Savage from Sloan Kettering. It was originally derived from a lymph node metastasis of a squamous cell carcinoma of the larynx in a 64 year old man. The cells grew as a monolayer and were routinely cultured in a 1:1 mixture of Dulbecco's modified Eagle medium and Harn's F12 medium supplemented with 10% fetal calf serum and gentamicin (50 $\mu$g/ml). Cells were passaged weekly using 0.125% trypsin-2 mM EDTA. Multicellular tumor spheroids (MTS) were initiated by plating logarithmic phase cells from monolayer cultures onto petri dishes coated with 1.25% agarose in normal medium (see Sacks, "Growth of Head and Neck Squamous Cell Carcinoma Cell Lines as Multicell Tumor Spheroids," Head and Neck Oncology Research Proceedings of the IInd International Head and Neck Oncology Research Conference, G. T. Wolf and T. E. Carey, ed., Kugler Publications, Amsterdam, pp. 3–9, 1987). Three days after initiation, small spherodal aggregates were transferred to spinner flasks and cultured at 37 degrees Celsius with medium changed every other day.

Spheroid Treatment by RA: For experimental chemical treatment of cancer, spheropids at Sloan Kettering were harvested from spinner flasks and desired sizes were selected by utilizing a stereoscopic microscope in a laminar flow hood. Approximately 600 uniformly sized spheroids were taken. Half of the spheroids were treated with retinoic acid (RA). The remainder served as controls and were treated with the vehicle dimethyl sulfoxide (DMSO) at a concentration of 0.1%. All manipulations with RA were performed under limited lighting. An equal volume of the Dulbecco's /f12/10% FCS/gentamicin medium was placed in each of the spinner flask. The spheroids were subsequently cultured at 37 degrees Celsius. Medium was changed every 48 hours, at which time the experimental and control spheroids were retreated with RA and DMSO respectively. On Day 10 the RA treated and untreated spheroids were harvested, washed with PBS, and subjected to fluorescence spectroscopy to determine differences between them. Mediscience Technology CD Scan Excitation and Fluorescence Spectrometer was used to measure the fluorescence spectra from both the chemical treated and control samples.

Frontal excitation was used to excite the MTS which had been placed in quartz cells. The samples were excited at various wavelengths and the resulting emission spectra were recorded. Using 320 nm excitation the spectra were measured from 320 nm to 580 nm. Similarly, excitation was performed at 340 nm with recording of the emission spectra between 360 and 660 nm. Excitation spectra at 340 nm and 450 nm were then recorded for exciting wavelengths from 200 to 320 nm and from 240 to 430 nm, respectively. The spatial size of the exciting beam was approximately 6x2 mm. The spectral intensity ratio, spectral profile, and spectral difference were measured to determine the differences between the treated and untreated spheroids. The ratio of intensities at 340 nm and 440 nm (from the emission scan excited by 300 nm) were calculated for each sample. This value has previously been shown to be useful in distinguishing between cancerous and benign tissues. Other pairs were selected and measured. These specific scans were chosen based upon our knowledge of spectral patterns of certain fluorophors (NADH, flavins, tryptophan, et al.) involved in emission and initial studies which determined these scans to be particularly useful in exploiting the spectral differences between RA treated and untreated spheroids.

Eleven paired sets of RA treated and control MTS were measured using fluorescence and excitation spectroscopic methods. Reproducible differences in spectral features associated with native fluorophors NADH, flavins, and tryptophan were found between control and experimental MTS treated for 10 days with RA ($10^{-6}$M). Spectral fingerprints obtained for control and treated samples were averaged, yielding a composite spectral pattern for each group. Significant differences were observed when 340 nm was used as an excitation wavelength. The NADPH band was monitored for change in electron transport in the RA treated samples.

(1) Fluorescence spectra excited at 340 nm

The averaged fluorescence spectral profiles (360 nm to 660 nm) excited by 340 nm are different for RA treated MTS and untreated MTS, as shown by curves a and b, respectively, of FIG. 1. The fluorescence spectral peak of the RA treated MTS, located at 457.8 nm, is shifted towards longer wavelengths by 6.5 nm when compared to the control MTS which has its peak at 451.3 nm. The spectral bandwidth of the, RA treated MTS is 119.0 nm and is 19.6 nm wider than that of the control (99.4 nm). A difference spectrum was generated and is displayed in FIG. 1(*a*), the spectrum being obtained from the fluorescence spectrum of the treated MTS minus the untreated MTS spectrum when both were normalized to the same intensity. The spectroscopic difference of the profiles of the RA treated MTS from the control spheroids is associated with an increase of flavins (spectral peak is about 530 nm) relative to NADH (spectral peak is about 450 nm) found in the RA treated MTS. The spectroscopic method can be used to see changes in chemical treated cancers.

(2) Excitation spectra emitted at 450 nm

Figure 2:
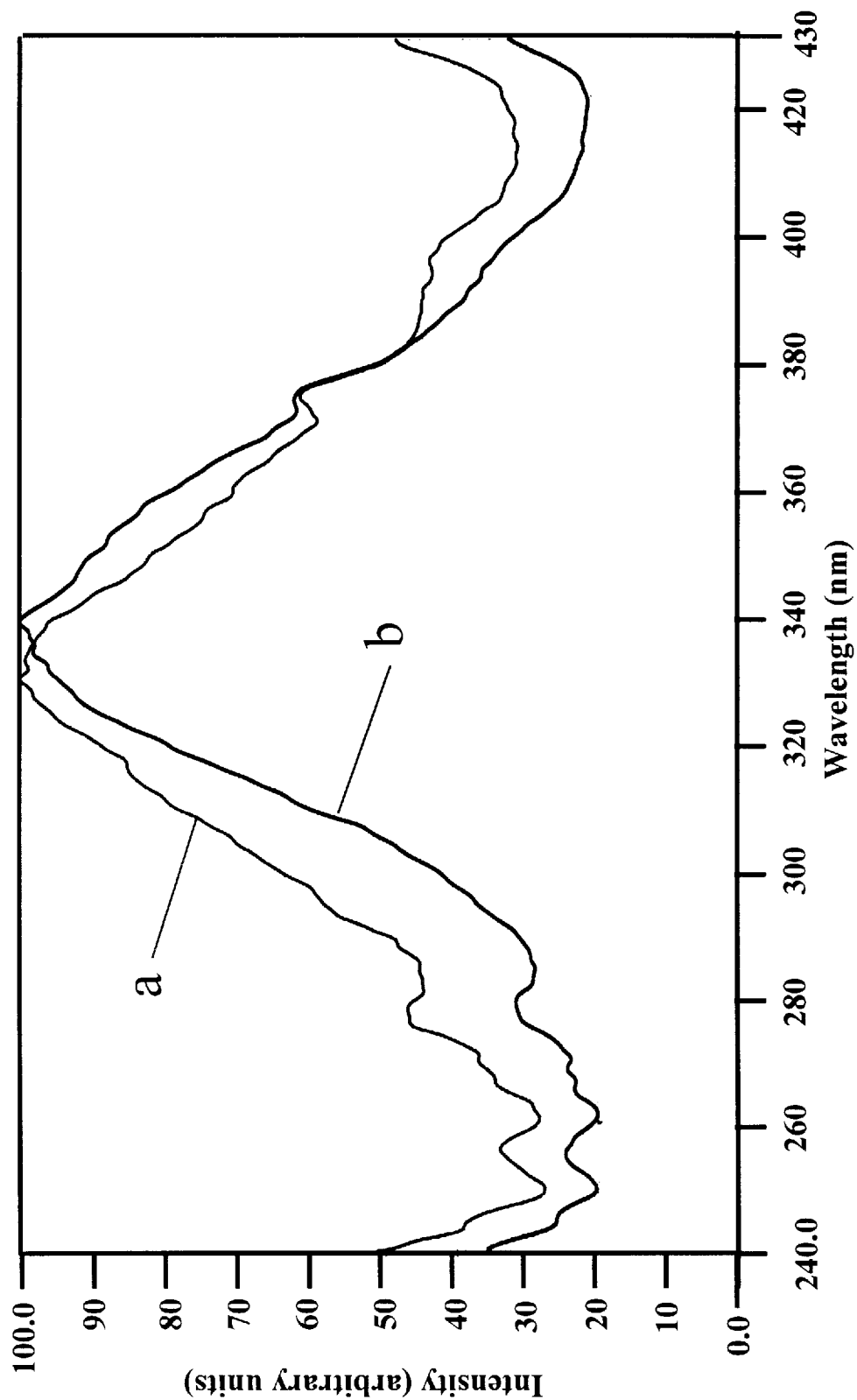
FIG. 2 is a graphic representation of the excitation spectra measured at 450 nm from the RA treated MTS (curve a) and from the control MTS (curve b)
Figure 2A:
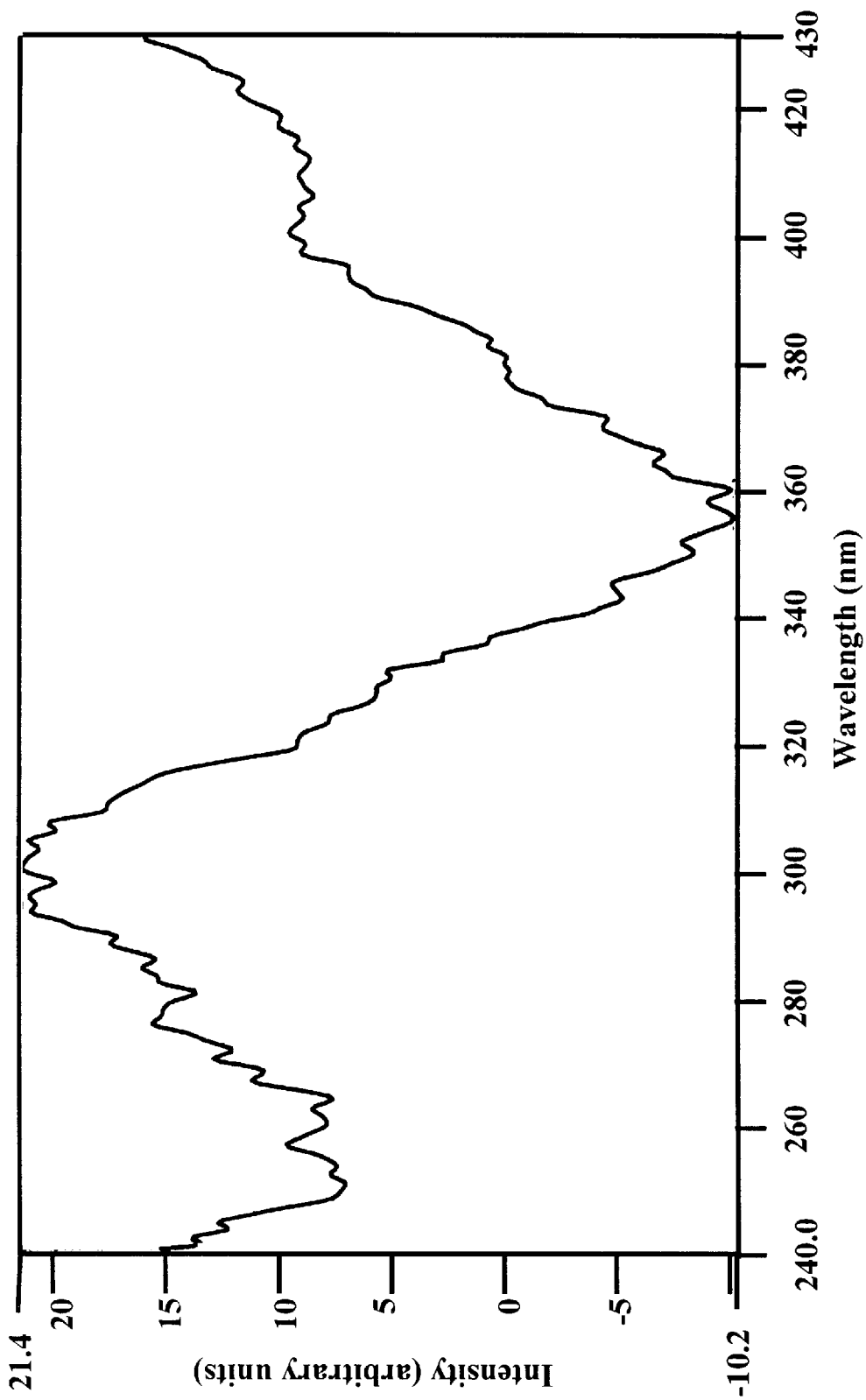
FIG. 2(a) is a graphic representation of the difference between curves a and b of FIG. 2 after they have been normalized to the same intensity.

The excitation spectra from the RA treated and control MTS were measured at the emission wavelength of 450 nm which is near to the fluorescent peak of RA treated and control spheroids. Typical averaged excitation spectral profiles of the RA treated and control MTS are shown in curves a and b of FIG. 2. The excitation spectral peak of the RA treated MTS is located at 327.7 nm which is shifted 14.6 nm to shorter wavelengths when compared to the control (peak at 342.3 nm). The excitation spectral bandwidth of the RA treated MTS is 130.4 nm which is 13.1 nm wider than that of the control (117.3 nm). A difference spectrum was generated and is displayed in FIG. 2(a), the difference spectrum being obtained from the excitation spectra of the RA treated MTS minus the control MTS excitation spectrum of FIG. 2. The spectroscopic difference of the RA treated from the control spheroids may reflect either an increase in relative number of NAD+ (oxidized, does not absorb or fluoresce) relative to NADH (reduced) for the RA treated MTS, or a change in the nonradiative rates for NADH. This result may reflect a change in electron transport in the production of ATP in the RA treated MTS.

(3) Excitation spectra emitted at 340 nm

Figure 3:
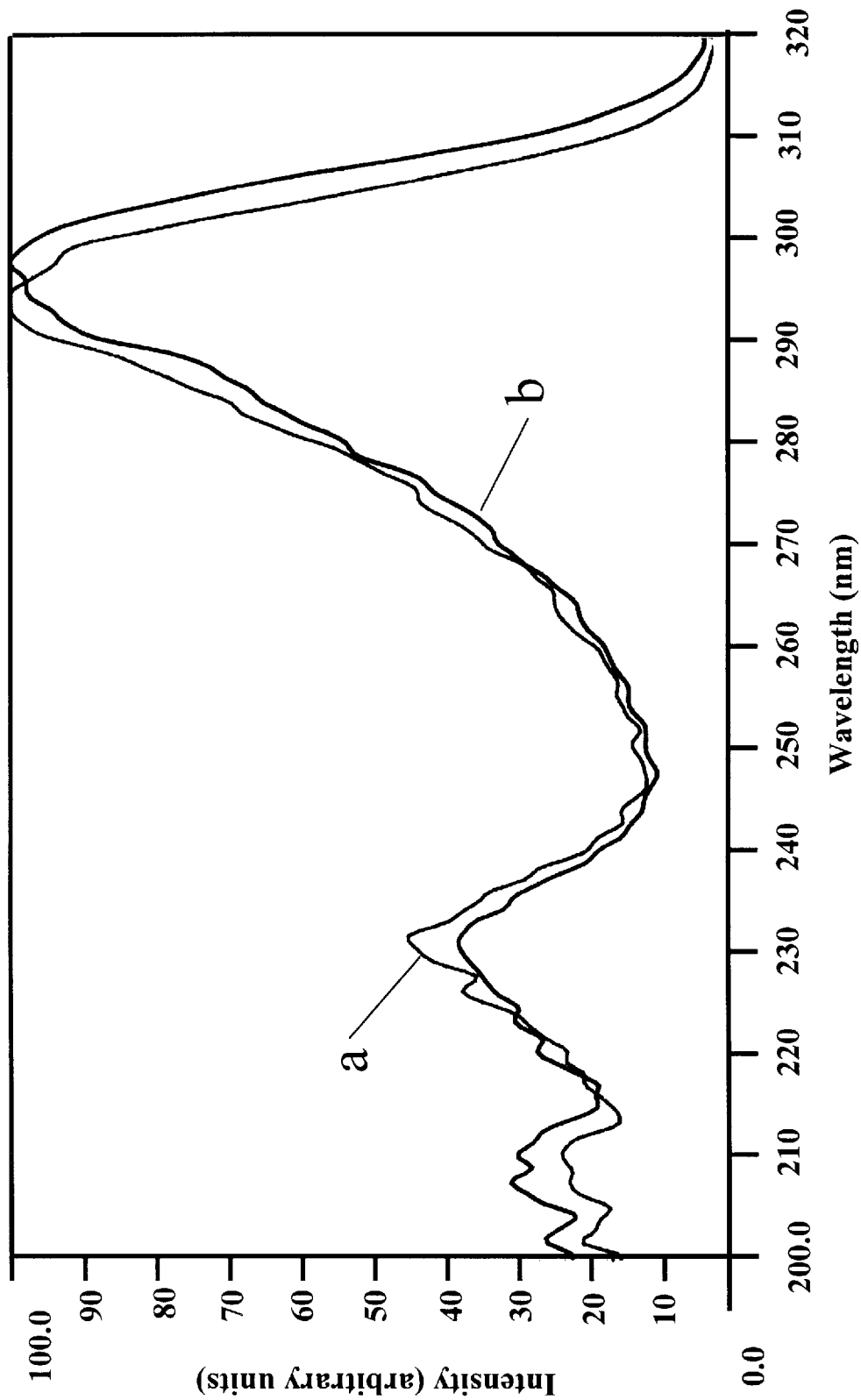
FIG. 3 is a graphic representation of the excitation spectra measured at 340 nm from the RA treated MTS (curve a) and from the control MTS (curve b)
Figure 3A:
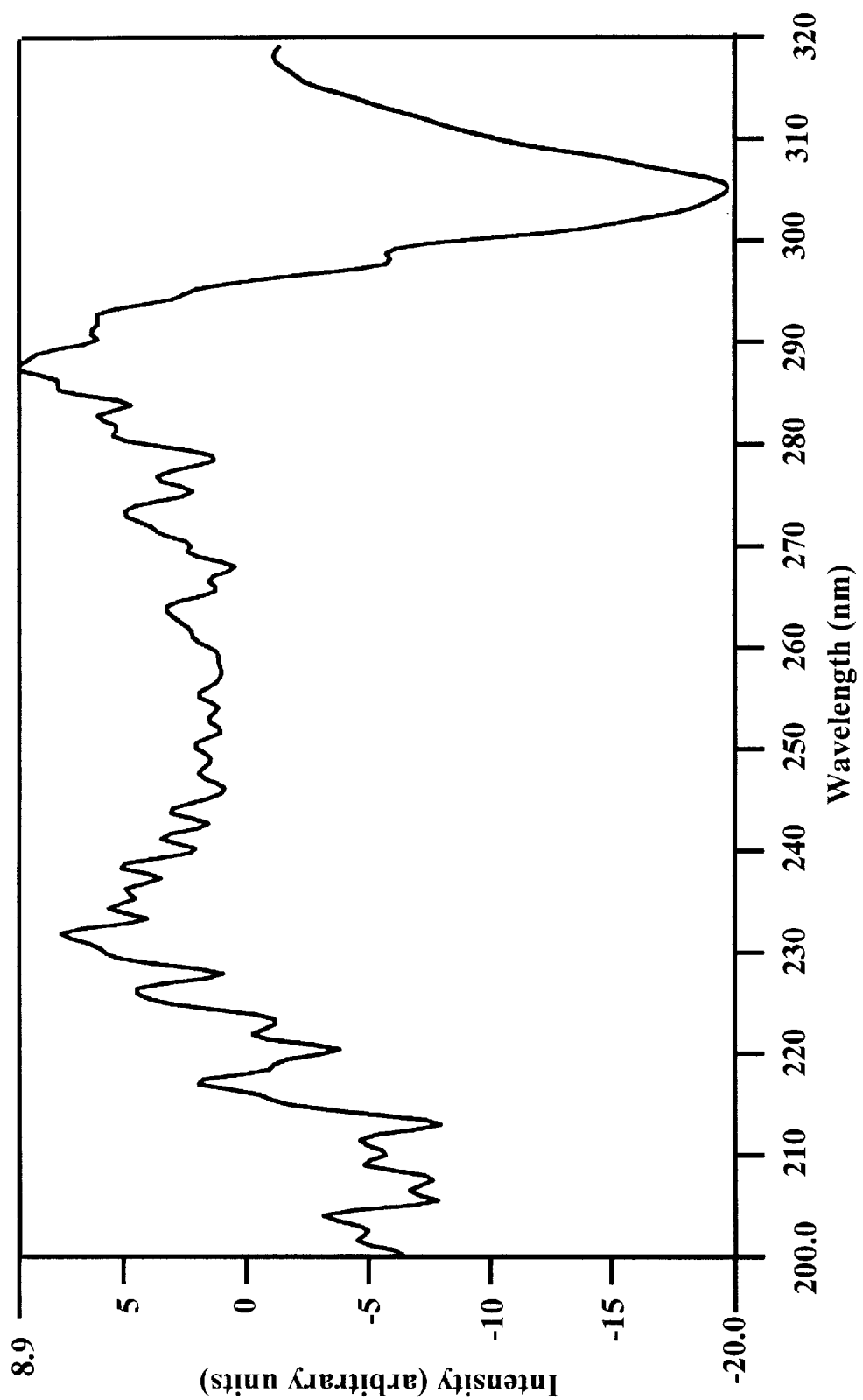
FIG. 3(a) is a graphic representation of the difference between curves a and b of FIG. 3 after they have been normalized to the same intensity.

The excitation spectra from the RA treated and control MTS were measured at the emission wavelength of 340 nm which is near to the fluorescence peak of tryptophan. Curves a and b of FIG. 3 show the averaged excitation spectra for the RA treated and control MTS, respectively. The excitation spectral peak of the RA treated MTS is located at 294.4 nm which is shifted 4 nm to shorter wavelengths when compared to that of the control MTS (298.4 nm). The excitation spectral bandwidth of the RA treated MTS is 28.45 nm which is 0.55 nm narrower than that of the control MTS (29.1 nm), but is under the measurement error (±2 nm). A difference spectrum was generated and is displayed in FIG. 3(a), the spectrum being obtained from the excitation spectrum of the RA treated MTS of FIG. 3 minus the control MTS excitation spectrum of FIG. 3. The difference spectrum which has a peak at 306 nm shows a decrease in the spectrum from these molecules treated by RA relative to the control MTS. This result indicates either a decrease of the number of tryptophan molecules or an increse in the nonradiative rates for the RA treated MTS relative to the untreated. This result may reflect a loss of biosynthesis of proteins in the RA treated cells. The loss in tryptophan and ATP molecules may be contributing to an inceease in biosynthesis of flavin (FAD). This result suggests that the action is probably occurring in mitochondria of cells.

(4) Fluorescence spectra excited at 300 nm

Figure 4A:
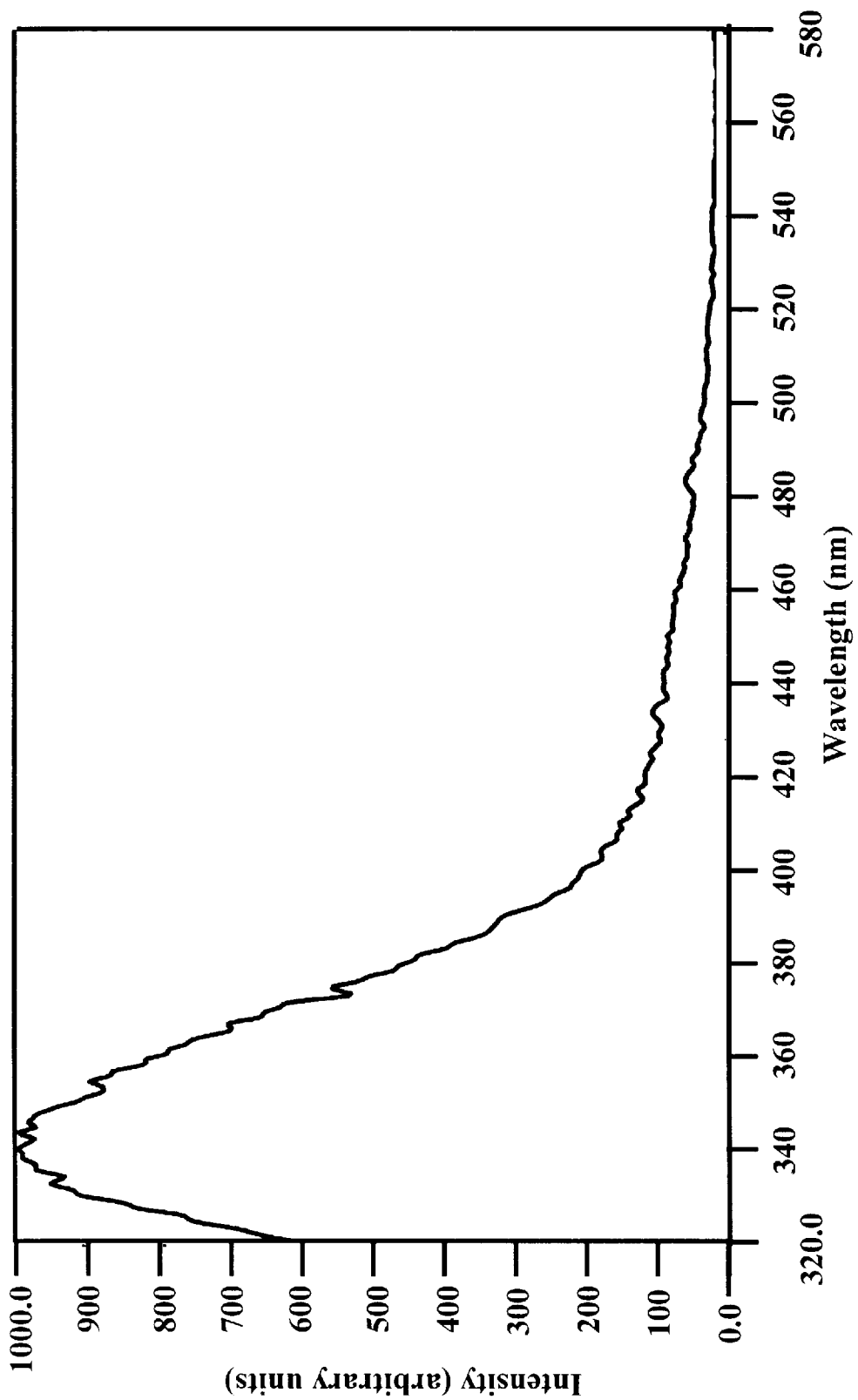
FIG. 4(a) is a graphic representation of the fluorescence spectrum obtained by exciting the RA treated MTS with 300 nm light.
Figure 4B:
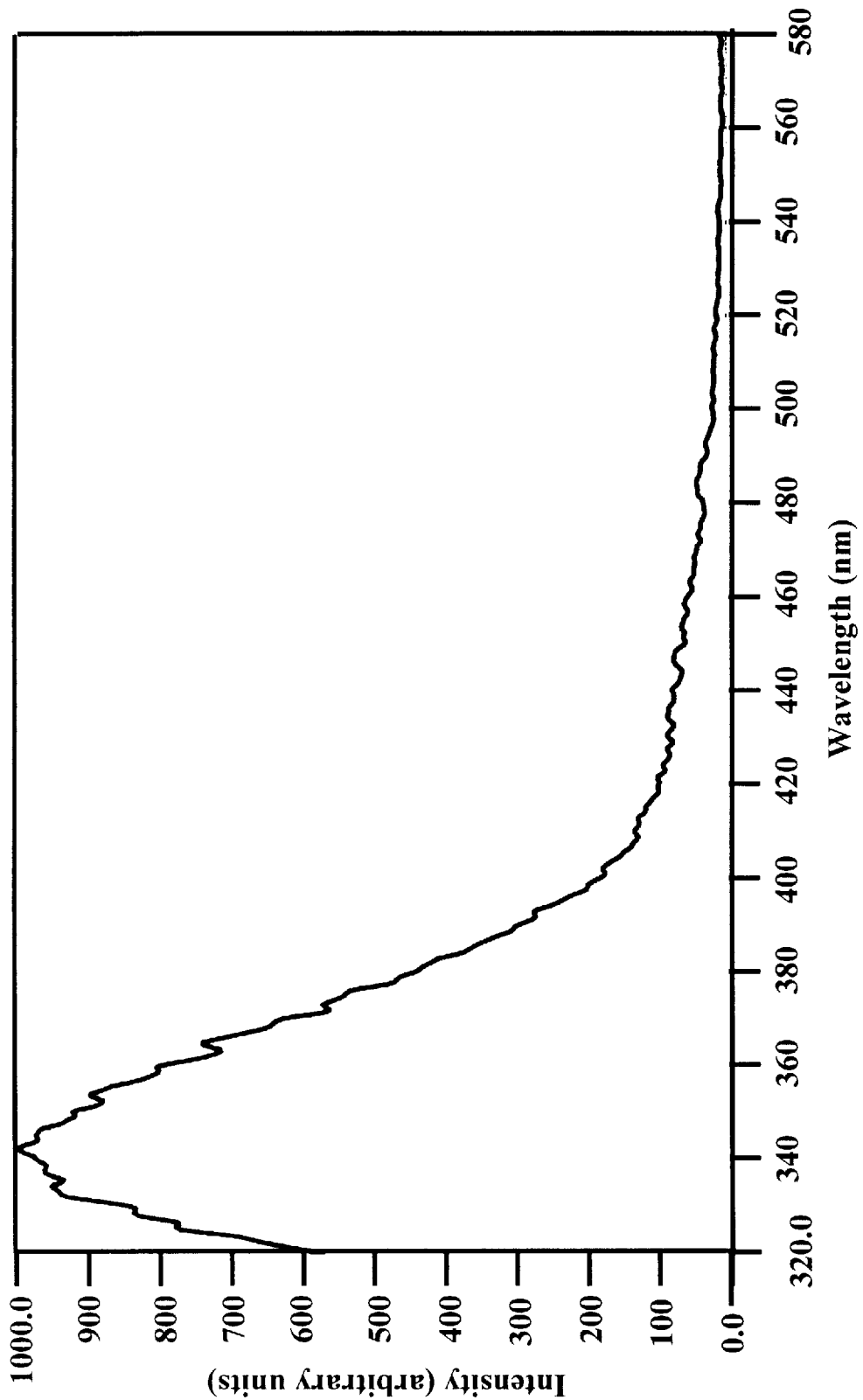
FIG. 4(b) is a graphic representation of the fluorescence spectrum obtained by exciting the control MTS with 300 nm light.

The fluorescence spectra excited at 300 nm were measured for the RA treated and the control MTS. The typical fluorescence spectral profiles are shown in FIG. 4(a) for the RA treated MTS and in FIG. 4(b) for the control MTS. The fluorescence spectral profile of the RA treated MTS is similar to that of the control MTS, and has a main peak located at 340 nm. However, a statistical study of the ratios of the fluorescence intensity at 340 nm to that at 440 nm shows that the ratios of the RA treated MTS were larger than 12 in region from 12 to 16, and the ratios of the control MTS were smaller than 12 in region from 10 to 12. In 10 control MTS samples and 11 measurements, all the ratios were larger than 12. 14, and in 8 RA treated MTS samples and 10 measurements, only one ratio was bigger than 12. The effect that the ratio of the RA treated MTS is larger than that of the control MTS, although the difference between both is not very large, will give one a powerful reference to detect the RA therapeutic effect in cancers.

As can be seen, significant fluorescence spectral differences were observed in the fluorescence spectroscopy patterns of the RA treated MTS when compared to the control MTS assigning from NADH, flavins, and tryptophan. Optical spectroscopy can be used in determining molecular changes in cells caused by chemicals and other agents. Fluorescence spectroscopy can be used as a biological marker to determine intermediate endpoints to evaluate the clinical use of chemical preventive cancer agents in therapy.

Figure 5:
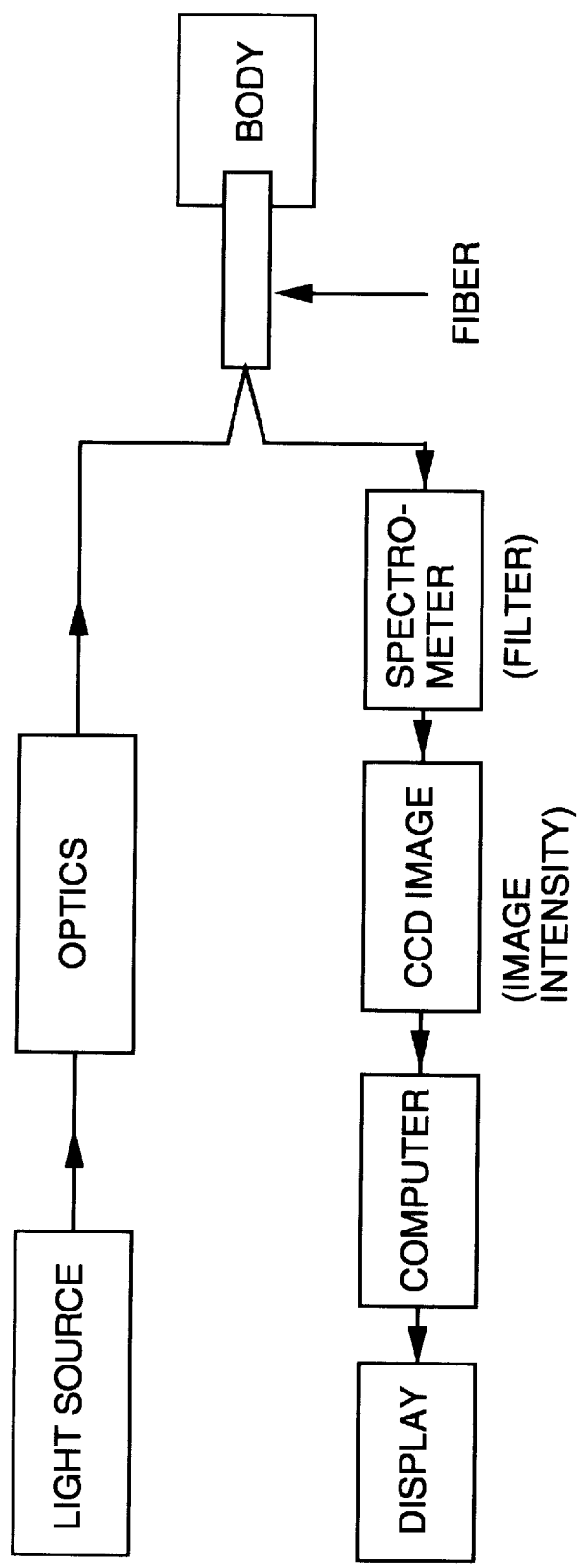
FIG. 5 is a schematic diagram of one embodiment of a system constructed according to the teachings of the present invention for monitoring the effects of a chemotherapeutic agent on a neoplasmic medium.

Referring now to FIG. 5, there is shown a fluorescence measuremental system which is used to study the RA treated and nontreated spheroids. This apparatus consists of a light source (a lamp or laser), optics (lens, filters, and mirrors), an optical fiber which is used to transmit the excitation light to the measured part of the body, a fluorescence collection fiber bundle which is bundled together with the transmiting fiber, a spectrometer (or color filters) to be used to measure the spectra from a diseased body part, a CCD detector (and/or a image intensifier) to be used to measure the spectral intensities, a PC computer to analyze the spectral data, and a display system to give a clinical report for a patient.

Figure 6:
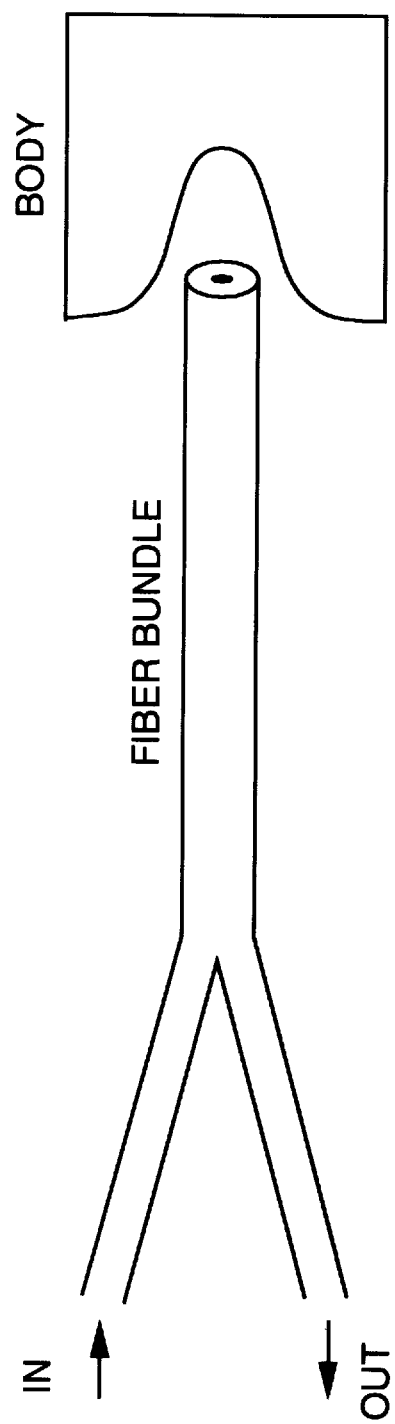
FIG. 6 is a schematic diagram of one type of optical fiber bundle arrangement which could be used in the system of FIG. 5.

FIG. 6 shows a type of optical fibers which is a fiber bundle included a light input fiber part and a fluorescent collection fiber part. This fiber bundle is used to measure the cancer disease on a body surface.

Figure 7:
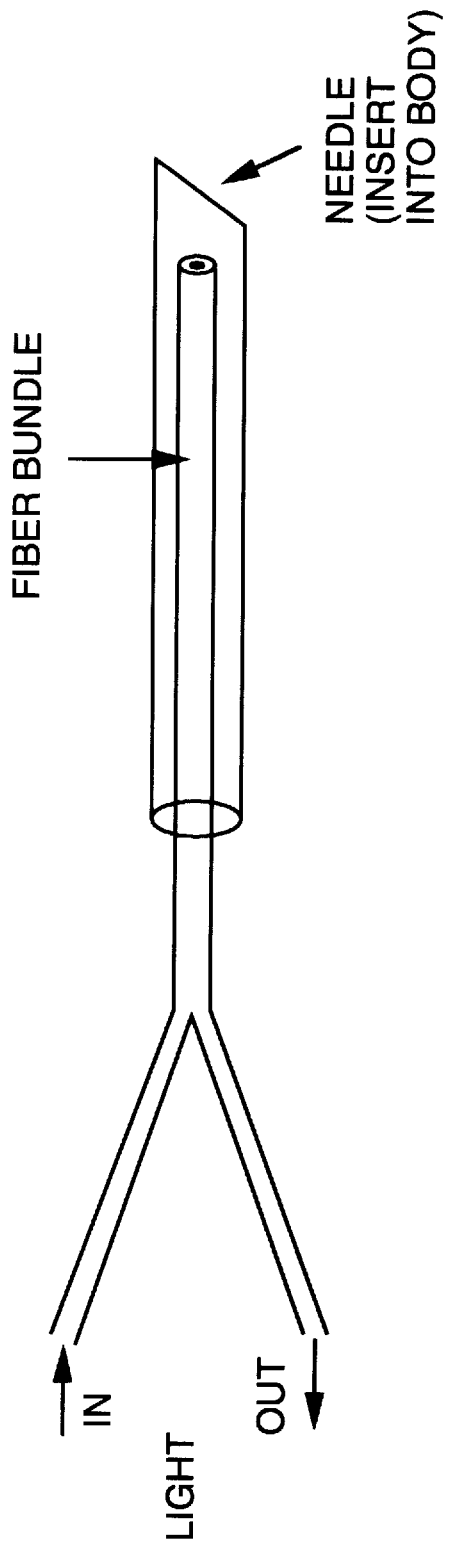
FIG. 7 is a schematic diagram of another type of optical fiber bundle arrangement which could be used in the system of FIG. 5.

FIG. 7 shows a design for measuring therapy effectiveness by chemicals and drugs. In this design, an optical fiber bundle is put into a needle which can be inserted into a body to excite and measure the fluorescence spectra of treated region.

Figure 8:
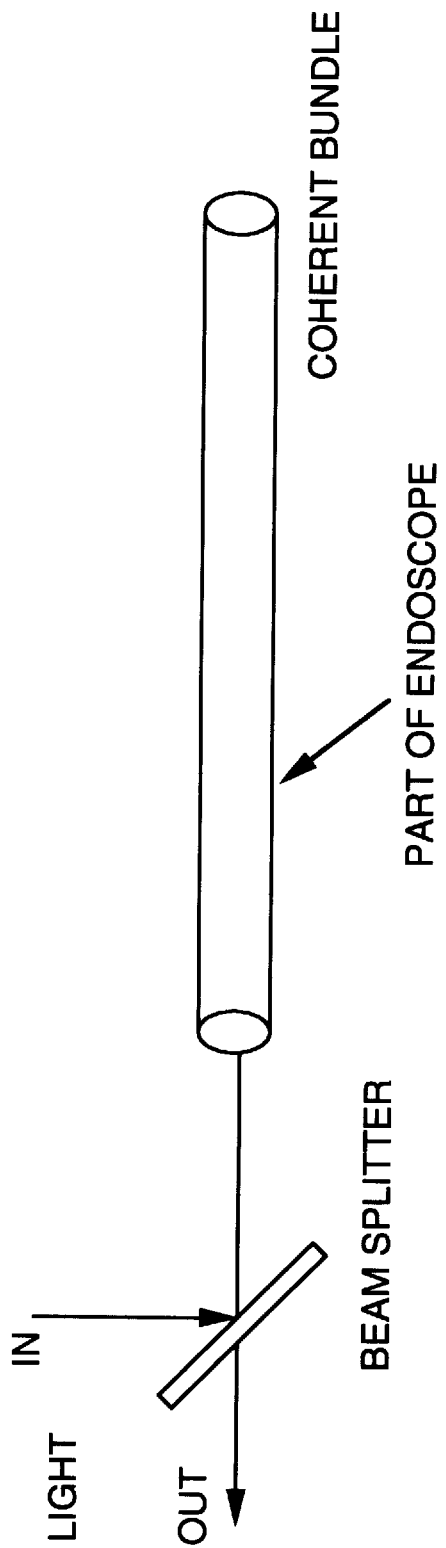
FIG. 8 is a schematic diagram of a third type of optical fiber bundle arrangement which could be used in the system of FIG. 5.

FIG. 8 shows another type of optical fibers in which an optical fiber bundle is put into a endoscope to excite and measure the fluorescence spectra of treated region.

Figure 9:
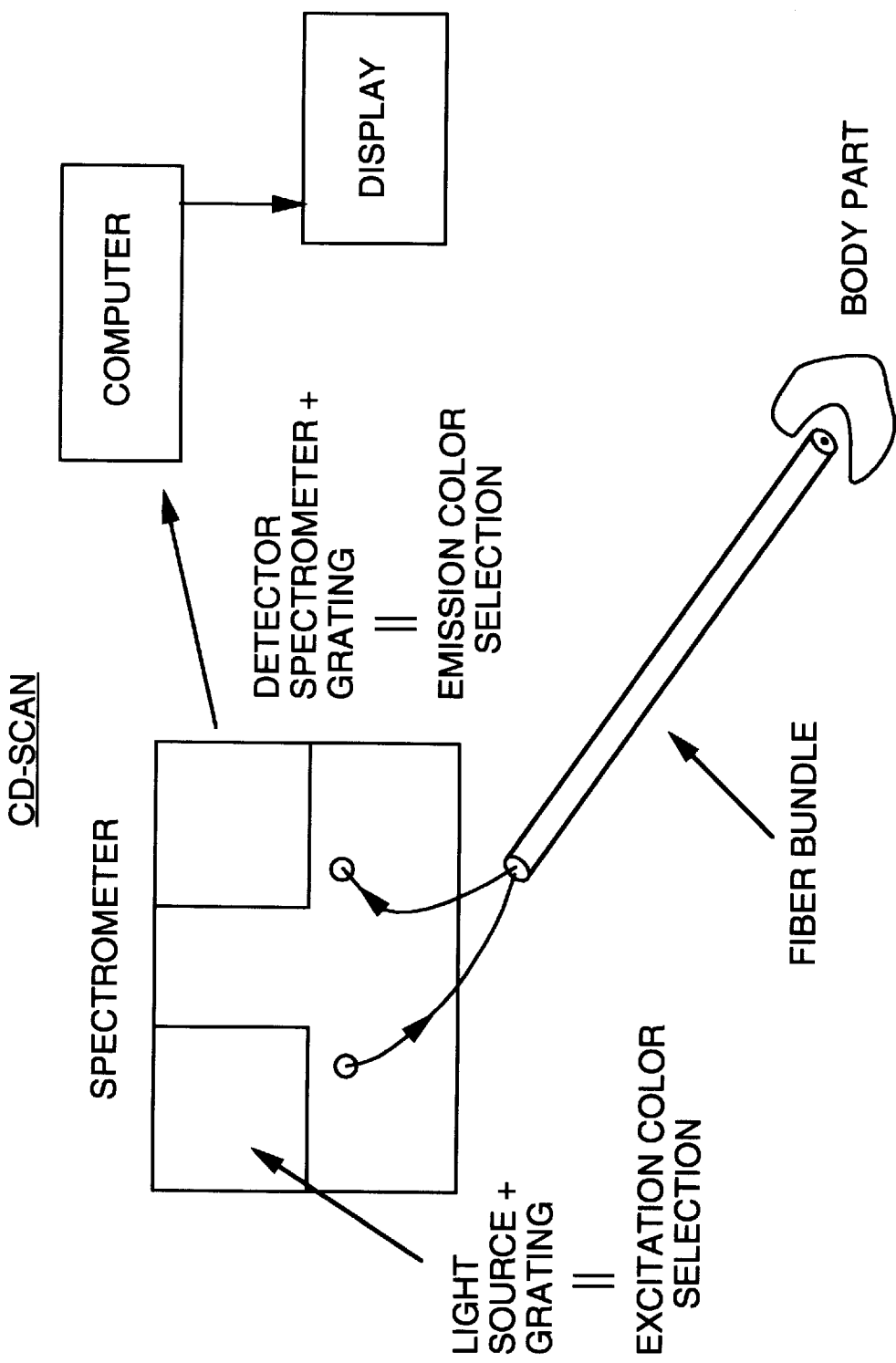
FIG. 9 is a schematic diagram of a second embodiment of a system constructed according to the teachings of the present invention for monitoring the effects of a chemotherapeutic agent on a neoplasmic medium.

FIG. 9 shows an excitation and emission spectrometer. The left part of the spectrometer is for the excitation wavelength selecting which consists of a light source and a grating. The right part of the instrument is for fluorescence measurements which consists of a grating and signal detector. An important part of this unit is an optical fiber bundle which is used to transmit the excitation light to a body part and collect the fluorescence from the body part. A PC computer and monitor are used to analyze and display the spectral data and to give a diagnosis report.

Figure 10:
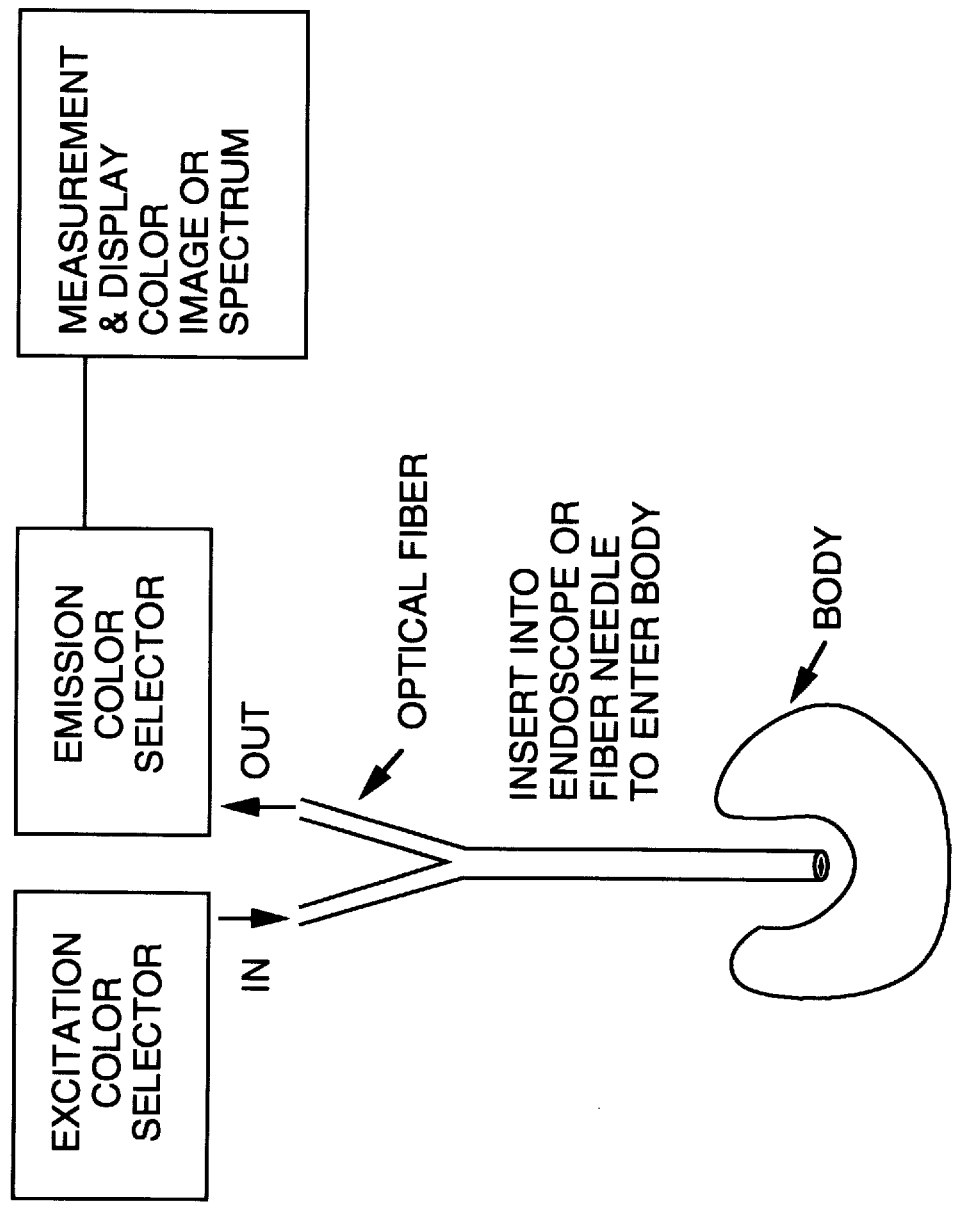
FIG. 10 is a schematic diagram of a third embodiment of a system constructed according to the teachings of the present invention for monitoring the effects of a chemotherapeutic agent on a neoplasmic medium.

FIG. 10 shows a design which is similar to FIG. 5. However, this design allows a doctor to determine the chemical or drug therapy effectiveness for cancer in the body. The optical fiber bundle is inserted into a endoscope or a needle which can enter a body to evaluate the tissue or organ state.

Figure 11:
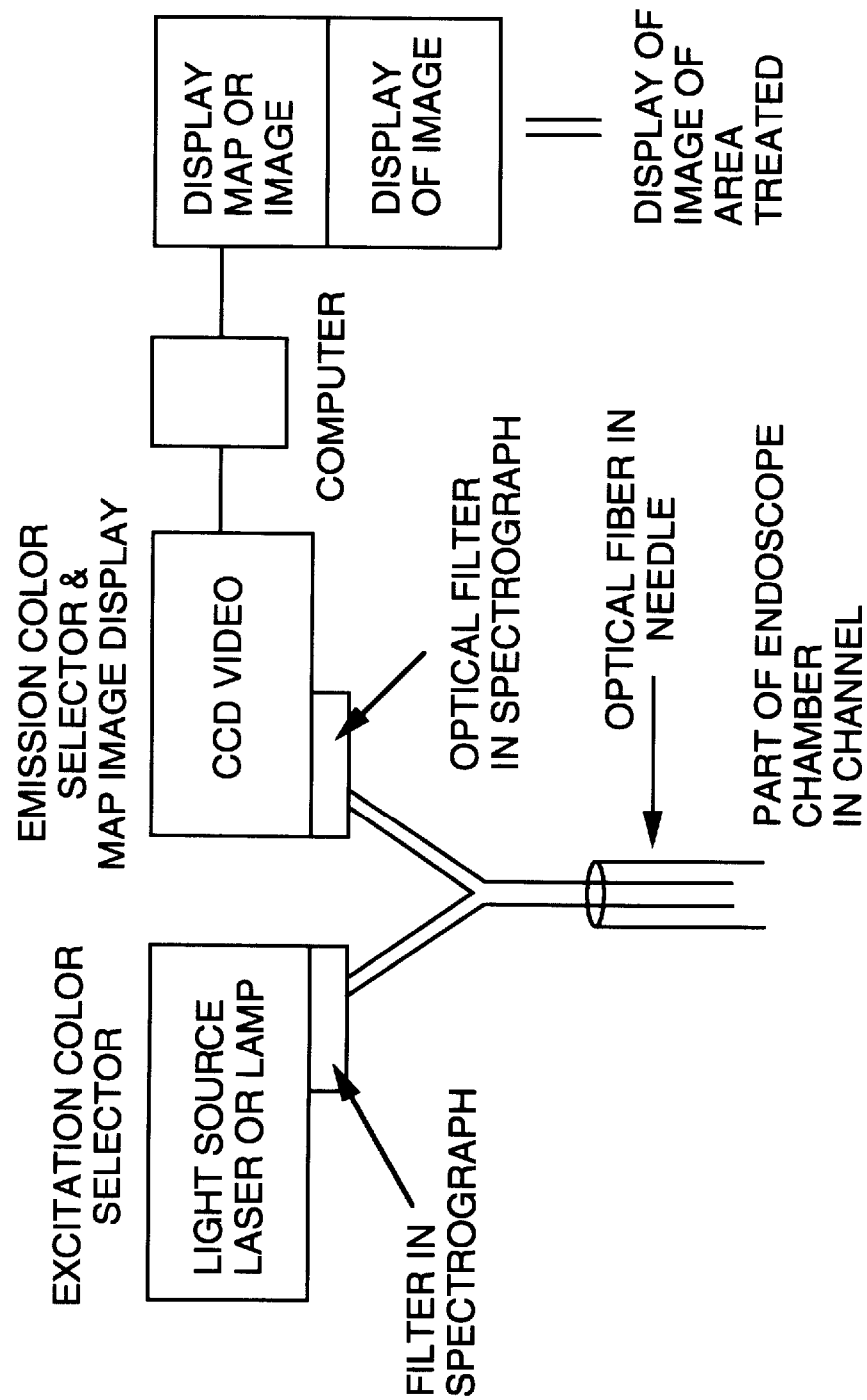
FIG. 11 is a schematic diagram of a fourth embodiment of a system constructed according to the teachings of the present invention for monitoring the effects of a chemotherapeutic agent on a neoplasmic medium.

FIG. 11 shows a fluorescence image system. The light source can be a laser or a lamp with filters or a spectrometer. The fluorescence wavelengths from a tissue or a tumor in body are selected by an optical filter or a spectrograph, and then enters an intensifier CCD video camera (cooled). Due to the fluorescence is coming from a section of a tumor, the video camera received an image of the section of the tumor. Changing color filter one by one on the filter wheel, one can obtain various fluorescence images for different wavelengths. A computer can measure the ratios of the intensities between two or more wavelengths one point by one point on all of the section. By doing so, one can get a map of ratios which can be used to detect the effectiveness of the cancer treated by chemicals or drugs.

Figure 12:
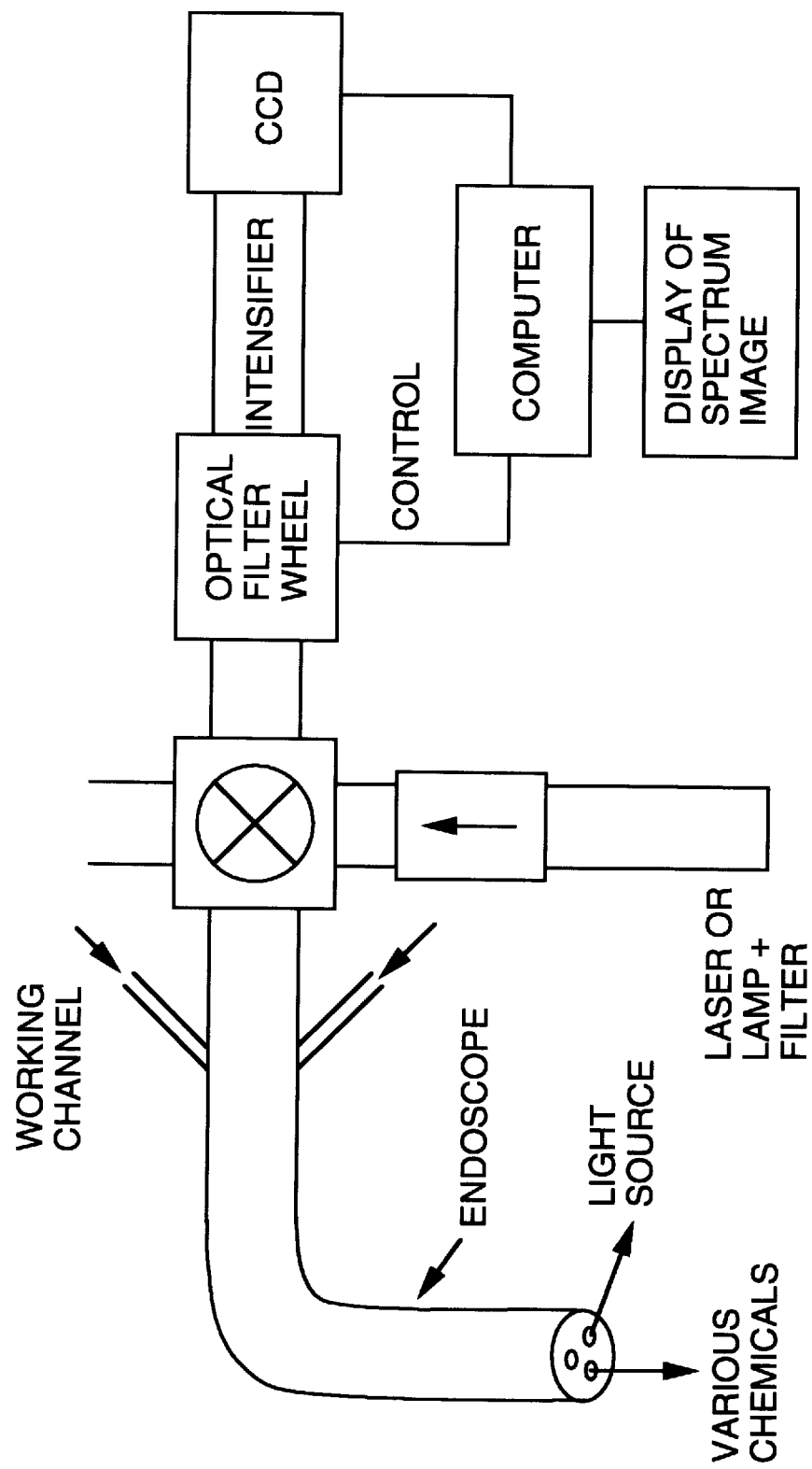
FIG. 12 is a schematic diagram of a fifth embodiment of a system constructed according to the teachings of the present invention for monitoring the effects of a chemotherapeutic agent on a neoplasmic medium.

FIG. 12 shows a design for a real time displaying system for cancer therapy being treated by chemicals or drugs. An endoscope with different channels included for the excitation light transmission, chemical injection and fluorescence collection can be used to do this work. The fluorescence passing through a spectral filter is measured by an intensifier and CCD detector system. The computer controls the optical filter wheel to select fluorescence wavelengths. After comparing the real time image with a normal tissue image which was stored in the computer before, the clinical report will be displayed on a monitor.

The following observations and features can be extracted from the discussion above:

1. The differences in the fluorescence spectroscopy in the spectral region from 320 to 660 nm were found between a control cancer model (the control MTS) and a chemical treated cancer model (the RA treated MTS). The differences include spectral profiles, spectral peaks, and spectral bandwidths of fluorescene at various wavelengths (two or more);

2. The differences in the excitation spectroscopy in the region from 200 to 460 nm were found between a control cancer model (the control MTS) and a chemical treated cancer model (the RA treated MTS). The differences include spectral profiles, spectral peaks, and spectral bandwidths of excitation spectra;

3. Fluorescence spectroscopy can be used as a reference to determine if changes in chemical and drug treated tissues is occuring;

4. The molecular changes of the chemical (RA) treated cancer (MTS) compared to the control (NMTS) normal organ were found. Tryptophan, NADH, flavins, et al. are involved these changes. Spectral changes from NADH, NADPH, collagen and elastin can be used as markers for chemical changes and cancer site changes;

5. Using an optical fiber bundle in an endoscope, the fluorescence spectroscopic methods can used as endpoints to evaluate the cancer states treated by chemicals and other agents;

6. Tissues and organs treated with chemical in vivo and in vitro can be evaluated by fluorescence spectral differences;

7. Using an optical fiber bundle in an endoscope, the excitation spectroscopic methods can be used as endpoints to evaluate the cancer states treated by chemicals and other agents;

8. Tissues and organs treated with chemical in vivo and in vitro can be evaluated by excitation spectra;

9. Spectral difference spectrum from a fluorescence spectrum of the RA treated MTS minus that of the control MTS can be used as biological end point markers of alterations in the cancer states;

10. The ratio of the fluorescence intensity at two or more wavelengths such as of 340 nm to that at 440 nm is an important biological marker to determine intermediate endpoints in clinical trials;

11. The effectiveness of chemical preventive agents in cancers can be evaluated using fluorescence and excitation spectroscopy. One can measure the spectral intensities, ratios, and differences at two or more wavelengths;

12. Changes in tissue and organ in body under chemical treatment can be detected using fluorescence and excitation spectroscopy;

13. Combining video system with filters to select wavelengths can be used with or without a endoscope to evaluate changes caused by chemicals in the cancer inside the body;

14. Fluorescence spectral changes from native molecules such as flavin, NADPH, NADH, tryptophan, collagen, elastin and other molecules in tissues and organs can be used to determine the effects of chemical preventive agent are affecting the cancer and if the chemicals are working to kill the cancer;

15. Using a fluorescence system for in vivo which consists of an image intensifier CCD video, a spectrometer or color filters or narrow band filters, a light source (laser or lamp with narrow band filter), coupled to a endoscope or a fiber bundle to enter the body, one can use a needle with this fiber bundle for excitation and collection of fluorescence signals;

16. Measure the fluorescence spectrum shape and intensity changes of the NADH or NADPH spectral band about 450 nm from the tissues to determine whether electron transport is inhibited or changed due to metabolic changes caused by using chemicals effecting on blood, oxygen, or nutrient supply to the tissue (such as hearts or other organs, tumors, neoplasia media);

17. Using a double or trifurcate optical fibers to couple to pump light into body to take the fluorescence image at two or various wavelengths, one can evaluate tissue status and determine a map of a cancer section of a tumor either treated with and without chemicals;

18. To measure spectral and intensity changes at several wavelengths to determine if chemical treatment is working or not to kill the cancer; and 19. Use video spectroscopy to map a fluorescence area of a tissue region chemical treated or nontreated to determine the effectiveness of the drug or chemical on cancer.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for monitoring the effect of retinoic acid on a neoplasmic medium, the method comprising the steps of:
   a) prior to administering retinoic acid to the neoplasmic medium, illuminating the neoplasmic medium with a beam of substantially monochromatic light;
   b) then, detecting fluorescent light emitted from the neoplasmic medium at one or more wavelengths;
   c) then, administering retinoic acid to the neoplasmic medium;
   d) then, illuminating the neoplasmic medium with said beam of substantially monochromatic light;
   e) then, detecting fluorescent light emitted from the neoplasmic medium at said one or more wavelengths;
   f) then, comparing the intensity of fluorescent light detected from the neoplasmic medium before and after administration of retinoic acid.

2. The method as claimed in claim 1 wherein said detecting steps comprise detecting the fluorescent light emitted from the neoplasmic medium over a broad spectral region and wherein said comparing step comprises comparing the fluorescence spectral profiles of said broad spectral region before and after administration of retinoic acid.

3. The method as claimed in claim 1 wherein said detecting steps comprise detecting the fluorescent light emitted from the neoplasmic medium over a broad spectral region and wherein said comparing step comprises comparing the fluorescence spectral peaks within said broad spectral region before and after administration of retinoic acid.

4. The method as claimed in claim 1 wherein said detecting steps comprise detecting the fluorescent light emitted from the neoplasmic medium over a broad spectral region and wherein said comparing step comprises comparing the fluorescence spectral bandwidths within said broad spectral region before and after administration of retinoic acid.

5. The method as claimed in claim 1 wherein said detecting steps comprise detecting the fluorescent light emitted from the neoplasmic medium at two wavelengths and wherein said comparing step comprises comparing the ratio of intensities at said two wavelengths before and after administration of retinoic acid.

6. The method as claimed in claim 1 wherein said detecting steps comprise detecting the fluorescent light emitted from the neoplasmic medium at two wavelengths and wherein said comparing step comprises comparing the difference of intensities at said two wavelengths before and after administration of retinoic acid.

7. The method as claimed in claim 1 wherein said beam of substantially monochromatic light has a wavelength of approximately 320 nm and wherein the fluorescent light emitted from the neoplasmic medium is detected at one or more wavelengths between about 320 nm and 580 nm.

8. The method as claimed in claim 1 wherein said beam of substantially monochromatic light has a wavelength of about 300 nm, wherein said detecting step comprises detecting the fluorescent light emitted from the neoplasmic medium at wavelengths of about 340 nm and at about 440 nm and wherein said comparing step comprises comparing the ratio or difference of intensities at about 340 nm and at about 440 nm before and after administration of retinoic acid.

9. The method as claimed in claim 1 wherein differences in the fluorescence of the neoplasmic medium before and after administration of retinoic acid can be used to indicate that changes have occurred in the neoplasmic medium due to the administration of retinoic acid.

10. The method as claimed in claim 9 wherein said differences in the fluorescence of the neoplasmic medium before and after administration of retinoic acid are caused by at least one of tryptophan, elastin, flavins, collagen, NADH, and NADPH.

11. The method as claimed in claim 1 wherein molecular changes in the neoplasmic medium due to the administration of retinoic acid thereto can be detected by fluorescence before structural changes in the neoplasmic medium can be detected.

12. A method for monitoring the effect of retinoic acid on a neoplasmic medium, the method comprising the steps of:
 a) prior to administering retinoic acid to the neoplasmic medium, illuminating the neoplasmic medium with a beam of substantially monochromatic light having a changeable wavelength over a spectrum of wavelengths;
 b) then, detecting fluorescent light emitted from the neoplasmic medium at a predetermined emission wavelength;
 c) then, administering retinoic acid to the neoplasmic medium;
 d) then, illuminating the neoplasmic medium with said beam of substantially monochromatic light having a changeable wavelength over said spectrum of wavelengths;
 e) then, detecting fluorescent light emitted from the neoplasmic medium at said predetermined emission wavelength; and
 f) then, comparing the intensity of fluorescent light detected from the neoplasmic medium before and after administration of retinoic acid.

13. The method as claimed in claim 12 wherein said illuminating steps comprise illuminating the neoplasmic medium with a beam of substantially monochromatic light over a broad spectral region, whereby an excitation spectrum is obtained, and wherein said comparing step comprises comparing the spectral profiles of the excitation spectra from the neoplasmic medium before and after administration of retinoic acid.

14. The method as claimed in claim 12 wherein said illuminating steps comprise illuminating the neoplasmic medium with a beam of substantially monochromatic light over a broad spectral region, whereby an excitation spectrum is obtained, and wherein said comparing step comprises comparing the spectral peaks of the excitation spectra from the neoplasmic medium before and after administration of retinoic acid.

15. The method as claimed in claim 12 wherein said illuminating steps comprise illuminating the neoplasmic medium with a beam of substantially monochromatic light over a broad spectral region, whereby an excitation spectrum is obtained, and wherein said comparing step comprises comparing the spectral bandwidths of the excitation spectra from the neoplasmic medium before and after administration of retinoic acid.

16. The method as claimed in claim 12 wherein said illuminating steps comprise illuminating the neoplasmic medium with a beam of substantially monochromatic light over the spectral region between about 200 nm and about, 320 nm and wherein said detecting steps comprise detecting the fluorescent light emitted from the neoplasmic medium at about 340 nm.

17. The method as claimed in claim 12 wherein said illuminating steps comprise illuminating the neoplasmic medium with a beam of substantially monochromatic light over the spectral region between about 240 nm and about 430 nm and wherein said detecting steps comprise detecting the fluorescent light emitted from the neoplasmic medium at about 450 nm.

18. A method for monitoring the effect of retinoic acid on a neoplasmic medium, the method comprising the steps of:
 (a) prior to administering retinoic acid to the neoplasmic medium, illuminating the neoplasmic medium with a beam of substantially monochromatic light, said beam of substantially monochromatic light having a wavelength of approximately 340 nm;
 (b) then, detecting fluorescent light emitted from the neoplasmic medium at one or more wavelengths between about 360 nm and 660 nm;
 (c) then, administering retinoic acid to the neoplasmic medium;
 (d) then, illuminating the neoplasmic medium with said beam of substantially monochromatic light;
 (e) then, detecting fluorescent light emitted from the neoplasmic medium at said one or more wavelengths between about 360 nm and 660 nm;
 (f) then, comparing the intensity of fluorescent light detected from the neoplasmic medium before and after administration of retinoic acid.

* * * * *